United States Patent
Togashi et al.

(10) Patent No.: US 9,782,383 B2
(45) Date of Patent: Oct. 10, 2017

(54) PROPHYLACTIC AND THERAPEUTIC AGENT FOR ATTENTION-DEFICIT/HYPERACTIVITY DISORDER

(71) Applicant: FUJIMOTO CO., LTD., Osaka (JP)

(72) Inventors: Hiroko Togashi, Hokkaido (JP); Sachiko Hiraide, Hokkaido (JP); Fumio Yoneda, Osaka (JP); Kazue Takahata, Osaka (JP)

(73) Assignee: FUJIMOTO CO., LTD., OSAKA (JP)

( * ) Notice: Subject to any disclaimer, the term of this patent is extended or adjusted under 35 U.S.C. 154(b) by 0 days.

(21) Appl. No.: 15/100,487

(22) PCT Filed: Dec. 15, 2014

(86) PCT No.: PCT/JP2014/083100
§ 371 (c)(1),
(2) Date: May 31, 2016

(87) PCT Pub. No.: WO2015/098591
PCT Pub. Date: Jul. 2, 2015

(65) Prior Publication Data
US 2016/0296495 A1 Oct. 13, 2016

(30) Foreign Application Priority Data
Dec. 25, 2013 (JP) .................. 2013-266498

(51) Int. Cl.
*A61K 31/00* (2006.01)
*C07D 307/00* (2006.01)
(Continued)

(52) U.S. Cl.
CPC .......... *A61K 31/343* (2013.01); *A61K 31/137* (2013.01); *A61K 31/138* (2013.01); (Continued)

(58) Field of Classification Search
CPC .... A61K 31/343; A61K 45/06; A61K 31/137; A61K 31/165; A61K 31/4168; A61K 31/4458; A61K 31/138
(Continued)

(56) References Cited

U.S. PATENT DOCUMENTS 6,391,914 B1* 5/2002 Knoll .................. C07D 307/81
514/469

OTHER PUBLICATIONS

Tsunekawa et al, Effects of ( R)-(-)-(benzofuran-2yl)-2-propylaminopentane hydrochloride[(-)-BPAP] in animal models of mood disorders, Behavioural Brain Research 189, 2008, p. 107-116.*

(Continued)

*Primary Examiner* — T. Victor Oh
(74) *Attorney, Agent, or Firm* — Wenderoth, Lind & Ponack, L.L.P.

(57) ABSTRACT

It is already known that 1-(benzofuran-2-yl)-2-propylaminopentane or a pharmacologically acceptable acid addition salt thereof exhibits an excellent effect as an antidepressant, a psychotropic drug, an antiparkinsonian drug, and an anti-Alzheimer's disease drug. However, it has not been known at all that the compound is effective for the prevention or therapy of attention-deficit/hyperactivity disorder (ADHD). The present invention has newly found that 1-(benzofuran-2-yl)-2-propylaminopentane or a pharmacologically acceptable acid addition salt thereof is effective for the prevention or therapy of ADHD, and has been accomplished.

4 Claims, 2 Drawing Sheets

(51) Int. Cl.
    *A61K 31/343*     (2006.01)
    *A61K 31/137*     (2006.01)
    *A61K 31/165*     (2006.01)
    *A61K 31/4168*     (2006.01)
    *A61K 31/4458*     (2006.01)
    *A61K 45/06*     (2006.01)
    *A61K 31/138*     (2006.01)

(52) U.S. Cl.
    CPC ........ *A61K 31/165* (2013.01); *A61K 31/4168* (2013.01); *A61K 31/4458* (2013.01); *A61K 45/06* (2013.01)

(58) Field of Classification Search
    USPC .......................................... 549/462; 514/17.5
    See application file for complete search history.

(56) References Cited

OTHER PUBLICATIONS

Surman, Evidence to Guide Treatment of Bipolar Disorder and Attention Deficit Hyperactivity Disorder,Medscape Multispecialty, May 31, 2007, p. 1-2.*

* cited by examiner

PROPHYLACTIC AND THERAPEUTIC AGENT FOR ATTENTION-DEFICIT/HYPERACTIVITY DISORDER

TECHNICAL FIELD

The present invention relates to a prophylactic and therapeutic agent for attention-deficit/hyperactivity disorder that comprises 1-(benzofuran-2-yl)-2-propylaminopentane or a pharmacologically acceptable acid addition salt thereof as an active ingredient.

BACKGROUND ART

The attention-deficit/hyperactivity disorder (hereinafter referred to as "ADHD" in some cases) is a neurodevelopmental disorder characterized by core symptoms of inattention and/or hyperactivity and impulsivity. The Diagnostic and Statistical Manual of Mental Disorders, 4th Edition, Text Revision (DSM-IV-TR) by the American Psychiatric Association describes that the estimated prevalence of this disease is 3 to 7% of school-aged children and 2 to 4% of adults, and the male-to-female ratio of the patients is from 2:1 to 9:1. According to an epidemiologic study based on the DSM-IV, the prevalence of ADHD symptoms in Japanese school-aged children is reported to be 5.6%. Also, in ADHD, comorbidity disorders such as learning disorder, depression, Asperger's syndrome, and oppositional defiant disorder are observed. Regarding neurobiological bases, it has been reported that ADHD patients have volume differences in brain regions such as the cerebellum, the splenium of corpus callosum, the cerebral cortex, the striatum, etc. (morphological anomalies) or imbalance in monoaminergic imbalance (functional anomaly), but details of the cause of the disease are unknown.

The pathogenesis of ADHD is reported that there is a link between a neurotransmitter dopamine and ADHD (Non-Patent Document 1). In studies on genetic factors for ADHD, dopamine-related genes such as dopamine transporter has been implicated.

It has been further reported on acquired factors such as perinatal factors or family environments and on involvement of various genes other than dopamine-related genes. Nowadays, therefore, it is considered that various neurochemical factors and environmental factors, in addition to a plurality of genetic predispositions, are involved complicatedly in the pathogenesis of ADHD (Non-Patent Documents 2 and 3).

ADHD has been treated by behavioral therapy (stimulation of social development) and medication therapy (control of symptoms). At present, the drugs used for the medication therapy are largely grouped into stimulants amphetamines including amphetamine, dextroamphetamine, and lisdexamfetamine, and methylphenidate, and non-stimulants atomoxetine, guanfacine and clonidine (in Japan, methylphenidate and atomoxetine are approved by the Government in 2013). The plasma membrane monoamine transporters in the brain are molecular targets of amphetamines, methylphenidate and atomoxetine.

At present, among approved medications for ADHD, methylphenidate has the highest effects and is used as the first-choice of medication treatment. Methylphenidate has high affinity for norepinephrine (NET) and dopamine transporters (DAT), and exerts its effect rapidly on the core symptoms.

However, even methylphenidate as the first-choice of medication has many ineffective or intolerant cases: it is reported to be ineffective for approximately three out of ten ADHD patients. Also, strong central stimulation and side effects including loss of appetite, headache, and insomnia are observed. Since many of ADHD patients are school-age children, there are concerns about adverse effects such as the risk of drug dependence and abuse due to long-term dosing. Moreover, since methylphenidate has only two types of available oral tablets, i.e., the immediate-release type and the sustained-release type, it cannot be administered so as to make the therapy of behavioral inhibition disorder (BID) effective in the main part of the awake time of the patient (Patent Document 2). Amphetamines such as amphetamine, dextroamphetamine and lisdexamfetamine, which are stimulants like methylphenidate, are used for the therapy of ADHD. However, these amphetamines with high potential for abuse are drugs under strict regulatory control as stimulants, and thus difficult in handling.

Atomoxetine is administered for cases where stimulants are ineffective or for patients who have risks of dependence and abuse, a comorbidity disorder and side effects.

Atomoxetine has highly selective affinity to NET, less potential for abuse, and comparatively low incidence of serious adverse events. However, atomoxetine might result in maximum response at the dose of once or twice a day over several weeks. Also, clinical trials are suggested that the atomoxetine's efficacy [effect size as the magnitude of improvement effect based on the ADHD Rating Scale total score=(average value of drug-treated group−average value of control group)/standard deviation of control group] is weaker compared with that of methylphenidate. Atomoxetine is therefore selected for ineffective cases with stimulants, the cases where the risk of dependence/abuse is concerned, and the cases where a side effect, a comorbid disorder, etc. are concerned.

While atomoxetine can improve the ADHD symptoms and is low in the possibility of dependence formation and frequency of adverse events based on the central stimulation action, which are feared for methylphenidate, the weak efficacy and slow onset of drug efficacy form a clinical bottleneck. Moreover, although atomoxetine is considered lower frequency of adverse events than methylphenidate, adverse events still manifest with high frequency: adverse events are reported in 209 subjects out of 278 safety-evaluated subjects (75.2%) in a clinical trial for children in Japan, where common adverse events include headache (22.3%), decreased appetite (18.3%), somnolence (14.0%), abdominal pain, (12.2%), and nausea (9.7%), and in 315 subjects out of 392 safety-evaluated subjects (including 278 Japanese patients) (80.4%) in a clinical trial for Japanese and Asian adults, where main symptoms include nausea (46.9%), decreased appetite (20.9%), somnolence (16.6%), dry mouth (13.8%), and headaches (10.5%) (prescription drug package inserts). Also, in ADHD model rats or normal rats, while methylphenidate exhibits dose-dependent increases in locomotor activities, atomoxetine does not exhibit increases in locomotor activities irrespective of increases in doses, and exhibit decreases in locomotor activities during an exploration period.

Guanfacine and clonidine, which have different pharmacological actions from drugs having affinity for monoamine transporters as those described above, exert efficacies via the presynaptic and postsynaptic $\alpha_2$ adrenoceptor agonistic action, but their efficacies thereof in extended formulation is shown to be equivalent to that of atomoxetine. When the effects of existing ADHD medications are insufficient, mood-stabilizers, antidepressants, antipsychotics, anti-anxiety medications, etc. are prescribed according to the symptom. However, since no therapeutic algorism according to the ADHD clinical state has been made, their effects on the core symptoms are only partial.

Bupropion is one of antidepressants acting as a norepinephrine and dopamine reuptake inhibitor (NDRI), and is prescribed, as optional treatment, for an ADHD patient for whom neither methylphenidate nor atomoxetine is effective, or for a type of patient whose condition is rather worsened with methylphenidate or atomoxetine. However, in this case, also, the efficacy of improving the core symptoms of ADHD is still insufficient.

PRIOR ART DOCUMENTS

Patent Documents

Patent Document 1: Japanese Patent Publication No. 2003-89643
Patent Document 2: Japanese Patent Publication No. 2013-56944

Non-Patent Documents

Non-Patent Document 1: Swanson J M et al., Neuropsychology Review 17:39-59 (2007)
Non-Patent Document 2: Franke B et al., Human Genetics 126:13-50 (2009)
Non-Patent Document 3: Diagnosis/Therapy Guideline of Attention-Deficit/Hyperactivity Disorder (ADHD), ed. by Kazuhiko Saito et al., Jiho, Inc., 3rd ed., 2008
Non-Patent Document 4: Shimazu S et al., Life Science, 72:2785-92 (2003)

SUMMARY OF THE INVENTION

Problems to be Solved by the Invention

The existing ADHD therapeutic drugs have problems such as onset of side effects such as formation of drug dependence, insufficient effect during the awake time, and insufficient efficacy.

Solutions to the Problems

The present inventors have aggressively carried out behavioral and pharmacological examinations regarding the effects of many drugs on ADHD-like symptoms, using a subline of stroke-prone spontaneously hypertensive rats (SHRSP), SHRSP/Ezo (Japanese Journal of Pharmacology 82 (Suppl. 1): 230P (2000), Japanese Journal of Pharmacology 85 (Suppl. 1): 249P (2001)), as a model that better reflects the clinical symptoms of inattention, hyperactivity, and impulsivity, among ADHD model animals. As a result, the inventors have found that 1-(benzofuran-2-yl)-2-propylaminopentane (hereinafter referred to as a "compound for use in the invention" in some cases) has excellent action as a prophylactic or therapeutic agent for ADHD, and have succeeded in accomplishing the invention.

The present invention includes:
(1) a prophylactic or therapeutic agent for attention-deficit/hyperactivity disorder that comprises 1-(benzofuran-2-yl)-2-propylaminopentane or a pharmacologically acceptable acid addition salt thereof as an active ingredient,
(2) the prophylactic or therapeutic agent for attention-deficit/hyperactivity disorder described in (1), wherein 1-(benzofuran-2-yl)-2-propylaminopentane is (−)-1-(benzofuran-2-yl)-2-propylaminopentane,
(3) the prophylactic or therapeutic agent for attention-deficit/hyperactivity disorder described in (1) or (2), wherein the prophylactic or therapeutic agent is used in combination with one or more kinds of drugs selected from other prophylactic or therapeutic agents for attention-deficit/hyperactivity disorder,
(4) the prophylactic or therapeutic agent for attention-deficit/hyperactivity disorder described in (3), wherein the other prophylactic or therapeutic agents for attention-deficit/hyperactivity disorder used in combination include methylphenidate, atomoxetine, amphetamine, dextroamphetamine, lisdexamfetamine, guanfacine, clonidine, and bupropion,
(5) use of 1-(benzofuran-2-yl)-2-propylaminopentane or a pharmacologically acceptable acid addition salt thereof for prevention or therapy of attention-deficit/hyperactivity disorder, and
(6) a therapeutic method for attention-deficit/hyperactivity disorder including administering an effective dose of 1-(benzofuran-2-yl)-2-propylaminopentane or a pharmacologically acceptable acid addition salt thereof to a patient suffering from attention-deficit/hyperactivity disorder.

The compound for use in the invention is an existing compound represented by the following chemical structural formula (refer to International Publication WO 1999/007667).

This compound for use in the invention has the monoaminergic activity enhancing effect (catecholaminergic and serotonergic activity enhancer (CAE/SAE)) mediated by the enhancement of membrane potential-dependent exocytosis, which is different from substrate-type releasing effect of stimulants such as amphetamine on catecholamine, monoamine oxidase inhibitors, catecholamine reuptake inhibitors, etc. that have been used since before the compound becomes known. The compound therefore does not induce the excessive release of catecholamine and the amine depletion at the catecholamine nerve terminal. The compound little causes problems such as unusual increase in locomotor activity (excitatory action), side effects such as neural toxicity against central nerves, and impaired responsiveness to patients, and is known to exhibit excellent effects as a safe and useful antidepressant, psychotropic drug, antiparkinsonian drug, and anti-Alzheimer's disease drug. However, it is not known at all that the compound for use in the present invention is effective for prevention and therapy of ADHD.

It has become evident that the (−) substance in the R configuration of the compound for use in the invention has especially excellent pharmacological activity compared with the (+) substance in the S configuration or the racemic modification (International Publication WO 2000/026204), further has a use as a therapeutic agent for drug dependence (International Publication WO 2006/057211), has neuroprotective effects and anti-apoptosis actions or inhibiting apoptosis (Patent Document 1), and has activating actions on brain-derived neurotrophic factor (BDNF) signal, etc. (Non-Patent Document 4).

As the preparation method for the compound for use in the invention, known are the preparation method for the racemic modification (International Publication WO 1999/007667) and the preparation method for the (−) substance in the R configuration and the (+) substance in the S configuration (International Publication WO 2000/026204, International Publication WO 2001/007704, and International Publication WO 2007/001015).

Regarding the affinity for human monoamine transporters, the compound for use in the invention and methylphenidate have affinities higher in the order of DAT>NET>serotonin transporter (SERT): they have substantially equal affinities for NET/DAT, but the compound for use in the invention is higher in the affinity for SERT (SERT/DAT). Atomoxetine has affinities higher in the order of NET>SERT>DAT (Neuropsychopharmacology 27: 699-711 (2002)). From the difference in the relative ratio of the affinity for the monoamine transporters, it is suggested that the compound for use in the invention has a pharmacological spectrum or properties different from the existing ADHD therapeutic drugs.

From the experiments using SHRSP/Ezo rats conducted by the present inventors, the compound for use in the invention has exhibited improvement action for ADHD-like symptoms, showing the usefulness as an ADHD therapeutic drug. Moreover, while methylphenidate is ineffective for impulsivity in this model, the compound for use in the invention is shown to have a potential inhibiting effect on impulsivity from results in an elevated-plus maze test and of the inner zone spent time in an open field test. The effectiveness of the compound for use in the invention on impulsivity is also supported from the fact that the affinity of the compound for use in the invention for SERT, of which contribution to impulsivity is strongly suggested, is relatively high compared with that of methylphenidate. Furthermore, while BDNF heterozygous mice have shown increased impulsivity, the compound for use in the invention having the BDNF signal activating action has shown the possibility of an impulsivity control mechanism via a monoamine-independent mechanism.

From the facts that a high dose of the compound for use in the invention increases the spontaneous locomotor activity in normal rats and that the relative ratio of the affinity for DAT and NET is similar to that of methylphenidate, the compound for use in the invention exhibits an efficacy spectrum and rapid onset of action different from those of atomoxetine. From this result, it has become evident that the compound for use in the invention exhibits a degree of effectiveness equal to or higher than the existing drugs for hyperactivity, impulsivity, and inattentive behavior in the ADHD model animals SHRSP/Ezo rats.

Optically-active substances, the (−) substance in the R configuration and the (+) substance in the S configuration, are present in 1-(benzofuran-2-yl)-2-propylaminopentane as the compound for use in the invention. In the present invention, optically-active substances, racemic modifications, or mixtures thereof may be used, but the pure (−) substance in the R configuration is more preferable.

Examples of pharmacologically acceptable acid addition salts of the compound for use in the invention include addition salts of: inorganic acids such as hydrochloric acid, sulfuric acid, hydrobromic acid, nitric acid, and methanesulfonic acid; and organic acids such as gluconic acid, tartaric acid, maleic acid, fumaric acid, succinic acid, malic acid, citric acid, and mandelic acid.

For the compound for use in the invention, a free base or a pharmacologically acceptable salt can be used. Also, a salt may be maintained in the state of a free base, or a free base may be maintained in the state of a salt, in an administering agent using a normally used inorganic or organic pH adjuster. A mixture of a salt and a free base may also be used.

For example, when a salt of the compound for use in the invention is used as an active pharmaceutical ingredient, it can be included in the administering agent as a free base by adding a basic compound including inorganic bases such as potassium hydroxide, sodium hydroxide, calcium hydroxide, magnesium hydroxide, trisodium phosphate, and tricalcium phosphate and organic bases such as diethanolamine, triethanolamine, diisopropanolamine, and methylethanolamine, as a pH adjuster, before or after formulation. When an organic base is used as an active pharmaceutical ingredient of the compound for use in the invention, it can be included in the administering agent as a salt by adding an acid compound including inorganic acids such as hydrochloric acid, sulfuric acid, hydrobromic acid, nitric acid, and methanesulfonic acid and organic acids such as gluconic acid, tartaric acid, maleic acid, fumaric acid, succinic acid, malic acid, citric acid, and mandelic acid, as a pH adjuster, before or after formulation.

When the compound for use in the invention is used as a prophylactic or therapeutic agent for ADHD, it is prepared together with a carrier, an excipient, and any other pharmacologically acceptable additive, as needed. For the prophylactic or therapeutic agent for ADHD according to the invention, it is possible to use an additive commonly used in the formulation technology field, such as an excipient, a binder, a disintegrant, a lubricant, a colorant, a pH adjuster, a tonicity agent, a surfactant, a stabilizer, a flavoring agent, a fragrance, a sweetener, a solubilizing agent, and a fluidizer, for example. Such an additive may be used by an amount commonly used in the formulation technology field, and two or more kinds of such additives may be mixed as appropriate.

The prophylactic or therapeutic agent for ADHD according to the invention can be administered orally or parenterally in the form of a tablet, a pill, a capsule, a granule, a powder, a liquid, an injection, an ointment, an eye-drop, a suspension, an emulsion, a syrup, a lotion, a suppository, a poultice, a plaster, and a tape, using a normal formulation technique.

When the prophylactic or therapeutic agent for ADHD according to the invention is used as an oral administering agent, an excipient, a disintegrant, a binder, or a lubricant, for example, may be added/mixed to the agent, and compression molding and coating such as sugarcoating and enteric coating may be performed as needed, according to a known method, to form tablets, pills, capsules, granules, powders, etc. Examples of the excipient include lactose, starch, crystalline cellulose, etc. Examples of the disintegrant include starch, sodium hydrogen carbonate, carboxymethyl cellulose, etc. Examples of the binder include starch, hydroxypropyl cellulose, polyvinylpyrrolidone, carboxymethyl cellulose sodium, etc. Examples of the lubricant include stearic acid and its magnesium or calcium salt, talc, etc.

When the prophylactic or therapeutic agent for ADHD according to the invention is used as an intraoral administering agent, the form is not specifically limited as far as it is applicable in the oral cavity. An excipient, a binder, a disintegrant, or any other appropriate additive may be added to the agent, to form sublingual tablets, buccal tablets, ointments of an oleaginous type, an emulsion type, a water-soluble type, etc., troches, etc. Examples of the excipient include silicic anhydride, mannitol, sorbitol, anhydrous calcium phosphate, etc. Examples of the binder include tragacanth, sodium alginate, etc. Examples of the lubricant include stearic acid and its magnesium or calcium salt, talc, etc.

When the compound for use in the invention is formed into a suppository, the vehicle used may be any one that is normally used for suppositories. Examples of such a vehicle include oily vehicles and aqueous vehicles. Oily vehicles include medium-chain fatty acid ester triglyceride, glycerin fatty acid ester, cacao butter, laurin butter, beef fat, hard fat, etc., and aqueous vehicles include macrogol, polypropylene glycol, glycerin, etc.

When the prophylactic or therapeutic agent for ADHD according to the invention is used as a transdermal patch such as a tape, the adhesive used is desirably one that has adherence at normal temperature and is low in dermal irritation at the touch with the skin, such as (meth)acrylic adhesives, rubber adhesives, and silicone adhesives. Transdermal formulation such as a tape little causes an abrupt change in blood concentration, and thus is especially desirable when an effective dose is continuously administered stably for a long time.

When the prophylactic or therapeutic agent for ADHD according to the invention is used as an injection, a tonicity agent, a pH adjuster, a buffering agent, a chelate agent, a preservative, etc. may be added to the solvent, as needed, to form an intravenous, intra-arterial, intramuscular, intraperitoneal, or subcutaneous injection by an ordinal method. Examples of the solvent include an injection solvent, normal saline, a plant oil, polyethylene glycol, propylene glycol, etc. Examples of the tonicity agent include sodium chloride and dextrose. Examples of the pH adjuster include an alkaline or acidifying agent and a buffering agent. Examples of the buffering agent include acetate salt, citric salt, phosphoric salt, etc. Examples of the chelate agent include ethylene diamine tetra-acetic acid (EDTA), etc. Examples of the preservative include benzyl alcohol, methylparaben, etc. Such an injection can be arbitrarily housed in an ampule, an injector, or a glass or plastic vial, for example.

The dose may vary with the condition, age, weight, etc. of the patient, but normally 0.1 to 1000 mg, preferably 1 to 500 mg, per day for adults can be administered at a time or several, or administered once in several days.

Advantages of the Invention

The prophylactic and therapeutic agent for ADHD according to the invention has an efficacy spectrum different from the existing ADHD therapeutic drugs such as methylphenidate and atomoxetine, and is expected to expand the options of the drug therapy for ADHD by being used alone or in combination with other ADHD therapeutic drugs.

BRIEF DESCRIPTION OF THE DRAWINGS

Means±standard error (n=10 to 18), * ($p<0.05$), ** ($p<0.01$) vs. vehicle (alternation rate) or total arm entries in Y1 trial. The broken lines ( - - - - ) indicate the average values of the alternation rate and the number of entries in Wistar-Kyoto (WKY) rats as genetic control animals conducted separately.

Means±standard error (n=7), * ($p<0.05$), ** ($p<0.01$) vs. vehicle. The broken lines ( - - - - ) indicate the average values of the total crossings in the indicated range of times in WKY rats conducted separately.

Means±standard error (n=6 to 7), * ($p<0.05$), ** ($p<0.01$) vs. vehicle. The broken lines ( - - - - ) indicate the average values of the inner zone spent times and the inner zone spent times per total crossings in the indicated range of times in WKY rats conducted separately.

Means±standard error (n=8 to 9), * ($p<0.05$) vs. vehicle. The broken lines ( - - - - ) indicate the average values of the total number of arm entries, the rate of open arm entries, the open arm spent times, and the open arm spent times/total arm entries in WKY rats conducted separately.

Y1 in FIG. 1 represents the first trial. Y2 in FIG. 1 represents the second trial. * in FIGS. 1 to 4 represents a significant level $p<0.05$ and ** represents a significant level $p<0.01$. The columns in FIGS. 1 to 4 indicate that □ is the vehicle; ■ is methylphenidate at 1 mg; ▨ is BPAP at 0.01 mg/kg; ▨ is BPAP at 0.03 mg/kg; ▨ is BPAP at 0.1 mg/kg; and ▨ is BPAP at 0.3 mg/kg. Further, VEH and MPH in FIG. 4 represent vehicle (saline) and methylphenidate, respectively.

MODE FOR CARRYING OUT THE INVENTION

The invention will be further described hereinafter by use of experiments, etc. It should however be noted that the invention is not limited to the following experimental examples.

Example 1

1. Experimental Method

Spontaneous hypertensive rats (SHR) have been widely used as an ADHD animal model. It has become evident that SHR, established as an essential hypertensive model in 1963, exhibits behavioral similarities to the ADHD symptoms such as hyperactivity, impulsivity and inattention at the juvenile period. However, SHR do not fulfil the behavioral and pharmacological profiles of an animal model of ADHD. For instance, the ADHD-like behaviors do not show male preponderance in SHR, and the effective dose of methylphenidate is high. Although the gene and the chromosomal domain related to the ADHD-like behaviors observed in SHR have not yet been fully clarified, it has been suggested, from the analysis of the phenotype in sub-strains and congenic rats, that there is no correlation between the abnormal behavior and the hypertension. As other ADHD models, some models have been reported including neonatal rats injected 6-hydroxydopamine into the brain, DAT knockout mice, Naples high-excitability (NHE) rats. However, it cannot be said that any of these animal models has sufficient validity as an ADHD model judging from the expression of symptoms and the response to therapeutic drugs, etc.

In consideration of the above, the present inventors have studied the validity as an ADHD model using the stroke-prone spontaneously hypertensive rats (SHRSP) as a substrain of SHR. Among others, SHRSP/Ezo rats as a substrain of SHRSP isolated from SHR in 1974 is considered to be an ADHD model more reflecting the clinical features of ADHD from the facts such as that behavioral pharmacological features such as hyperactivity, impulsivity, and inattention during the juvenile period, that the male preponderance on the symptom is recognized, and that the effective dose of methylphenidate is close to the clinical dose range. In this experiment, therefore, the effects of the compound for use in the invention on the ADHD-like symptoms have been evaluated behavioral-pharmacologically using SHRSP/Ezo rats.

In all the tests described herein, the R configuration (−) substance hydrochloride salt of the compound for use in the invention (hereinafter referred to as "BPAP" in some cases) as the test material and methylphenidate hydrochloride (SIGMA Aldrich) as the comparative drug were dissolved in saline, diluted to a volume of 2 ml/kg before administration, and systemically administered into six-week-old male SHRSP/Ezo rats 30 minutes before behavior tests. Note that BPAP was subcutaneously (s.c.) administered, and methylphenidate was subcutaneously (s.c.) or intraperitoneally (i.p.) administered after the confirmation that there was no difference between the two routes, i.e., the s.c. and i.p. administration.

1) Evaluation of Inattentive Behavior in the Y-Maze Test

The short-term working memory was evaluated as a spontaneous alternation behavior using a Y-maze (45 (length)×10 (width)×35 cm (height)). The spontaneous alternation is a behavior based on the habit of a rodent preferring to investigate a new arm of the maze rather than returning to one that was previously visited in the Y-maze. In order to select three different arms continuously, it is necessary to remember the previously visited arm. To achieve this, therefore, the short-term working memory is considered indispensable. Because the processes of the short-term working memory are closely related to an appropriate amount of attention toward achievement of the task, the short-term working memory implicates aspects of attention. Thus, the Y-maze test was carried out to evaluate the inattentive behavior in SHRSP/Ezo rats.

The spontaneous alternation was measured according to the method by Sarter et al. (Psychopharmacology (Berl), 94:491-5 (1988)) using the following procedure. Under a 200-lux illuminance condition, each rat was placed in the center of the crossing point of the three arms and allowed to enter the maze arm freely for eight-minute test session, and the sequence of arm entries was recorded. The alteration behavior was defined as the consecutive entry into three arms, i.e. the combination of three different arms, with stepwise combinations in the sequence. The percentage obtained by dividing the spontaneous alternation behavior by the total number of arm entries (total arm entries) minus 2 was determined as the spontaneous alternation behavior rate (alternation rate). For example, assuming that the rat has entered the arms A, B, and C of the Y-maze in the order of ACBABACBAB, the spontaneous alternation behavior is five (ACB, CBA, BAC, ACB, and CBA), the total number of arm entries is ten, and the spontaneous alternation behavior rate is 62.5%. To consider the influence of variations in spontaneous alternation behavior rate among groups during the baseline (drug-untreated) period on the drug efficacy evaluation, the first Y-maze test was carried out three days before the drug efficacy evaluation, and grouping was performed based on the result of spontaneous alternation behavior rates in the $1^{st}$ Y-maze test.

2) Evaluation of Hyperactivity in the Open Field Test

The spontaneous locomotor activity in a new environment was evaluated using an open-field apparatus (90 (width)×90 (depth)×40 cm (height), 81 squares). Since an animal exposed to a new environment exhibits an exploration behaviors and rearing activities, the open field test is generally used for evaluation of the locomotor activity, emotionality, and general behaviors of animals.

In this experiment, under a 200-lux illuminance condition, rats were placed in the center of the open field and allowed to move freely in the field for a 60-minute test session, and the horizontal activities (crossings: the number of squares crossed) during the exploration was analyzed by a video tracking system for behavioral experiments (LimeLight Actimetrics, USA).

3) Evaluation of Impulsivity in the Elevated-Plus Maze Test

The anxiety-related behavior was evaluated using an elevated plus maze (open arm: 50 (length)×10 cm (width), enclosed arm: 50 (length)×10 (width)×40 cm (height), height above the floor: 50 cm). The device is constituted by a wall-less open arm and a wall-surrounding enclosed arm crossing each other at right angles at a height of 50 cm above the floor. An animal staying in an open arm is exposed to anxiety in the elevated wall-less open state. A normal animal therefore does not stay long in the open arm. The elevated-plus maze test reflects an equilibrium state between the approach behavior (curiosity) and the avoidance behavior driven by anxiety in an animal, and thus is generally used for the evaluation of the anxiety level of an animal. It is suggested that involvement of the anxiety level in impulsivity of ADHD patients, and thus the impulsivity is considered to embrace an aspect of having a reduction in anxiety level as the background.

In this experiment, under a 200-lux illuminance condition, a rat was placed in the center of the crossing point of two sets of arms and allowed to enter freely into the maze for a ten-minute test session. The total number of arm entries (total arm entries), the time spent in open arms and the rate of open arm entries were analyzed by a video tracking system for behavioral experiments (LimeLight Actimetrics).

4) Statistics Analysis

Data were represented as the means±standard errors. Student's t-test was used for the statistics analysis, and a P value below 5% was considered statistically significant.

2. Experimental Result

1) Validity of Dose of Methylphenidate, the First-Choice of Medication for ADHD, as Comparative Drug As a result of the evaluation of the spontaneous locomotor activity in the open field test, horizontal ambulatory significantly increased in SHRSP/Ezo rats at the habituated phases of 15 to 60 minutes, in comparison with Wistar-Kyoto (WKY) rats as genetic control animals. By contrast, at the exploration phase in the initial 0 to 15 minutes period, the horizontal ambulatory did not differ between SHRSP/Ezo and the WKY rats. The intraperitoneal administration of methylphenidate (0.01 to 30 mg/kg) significantly decreased the hyperactivity in SHRSP/Ezo rats at 0.01 and 0.1 mg/kg, but it did not decreased at 1 mg/kg. By contrast, the increase in spontaneous ambulatory was exacerbated with 3 and 30 mg/kg of methylphenidate.

In the evaluation of the impulsivity in the elevated-plus maze test, the number of open arm entries and the open arm spent time increased in SHRSP/Ezo rats, compared with those of the WKY rats. As for the number of enclosed arm entries, however, no difference was observed between SHRSP/Ezo and the WKY rats. The intraperitoneal administration of methylphenidate (0.01 to 1 mg/kg) provided no statistically significant change for the increase in the number of open arm entries and the extension of the open arm spent time in SHRSP/Ezo rats.

In the evaluation of the inattentive behavior in the Y-maze test, the spontaneous alternation behavior rate in SHRSP/Ezo rats significantly decreased compared with that of the WKY rats, indicating the impairment of a short-term memory including reduction in attention. Also, an increase in the total number of arm entries, i.e., hyperactivity was observed in SHRSP/Ezo rats. The intraperitoneal administration of methylphenidate (0.01 to 1 mg/kg) dose-dependently improved the reduction in spontaneous alternation behavior rate in SHRSP/Ezo rats. While 1 mg/kg of methylphenidate improved the reduction in spontaneous alternation behavior rate in SHRSP/Ezo rats, a significant exaltation in the increase in the total number of arm entries was observed. Methylphenidate at 0.01 and 0.1 mg/kg had no influence on the increase in the total number of arm entries in SHRSP/Ezo rats.

From the above results, SHRSP/Ezo rats, exhibiting ADHD-like symptoms such as hyperactivity, impulsivity, and inattention, was confirmed to have the face validity as an ADHD model. SHRSP/Ezo rats had also satisfied the prediction validity because methylphenidate was effective for such ADHD-like symptoms. As the dose of methylphenidate used as the comparative drug in the following evaluation of the effects of the compound for use in the invention, 1 mg/kg was determined with which an improvement in inattentive behavior was observed in the Y-maze test and the risk of worsening the hyperactivity was detectable.

Figure 1:
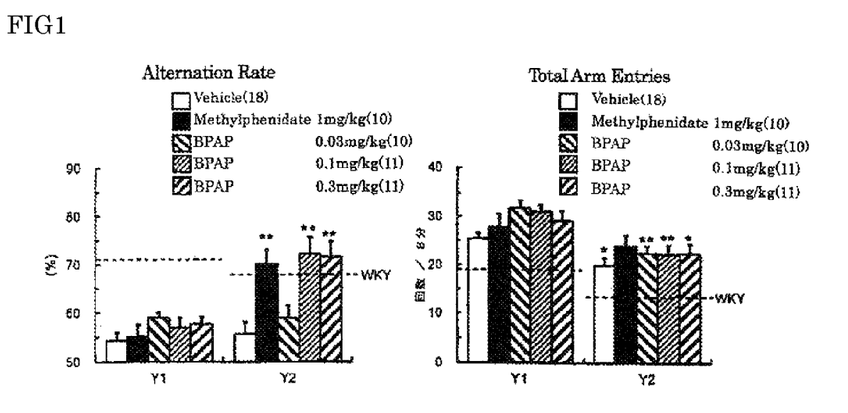
FIG. 1 shows the effects of the compound for use in the invention on the alternation rate (left) and the total arm entries (right) in SHRSP/Ezo rats in a Y-maze test.

2) Evaluation of Effects of Compound for Use in the Invention on Hyperactivity, Impulsivity, and Inattentive Behavior in SHRSP/Ezo Rats 2-1) Y-Maze Test As a result of the evaluation of the inattentive behavior in the Y-maze test, methylphenidate (1 mg/kg) recovered the reduction in spontaneous alternation behavior rate observed in SHRSP/Ezo rats without increasing the total number of arm entries. The subcutaneous administration of the compound for use in the invention (0.03 to 0.3 mg/kg) significantly improved the impaired alternation behavior in SHRSP/Ezo rats at 0.1 to 0.3 mg/kg, but no improvement action was observed at a dose of 0.03 mg/kg. Also, the compound for use in the invention at 0.03 to 0.3 mg/kg significantly decreased the total number of arm entries, compared with the first trial (Y1) (FIG. 1).

2-2) Open Field Test

Figure 2:
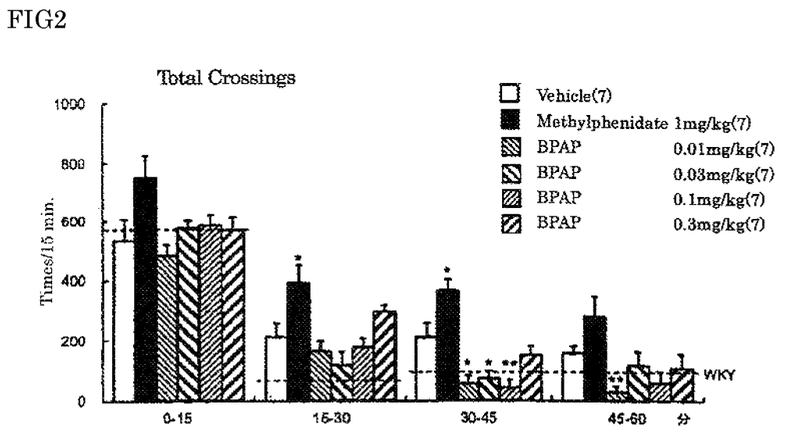
FIG. 2 shows the effects of the compound for use in the invention on hyperactivity in SHRSP/Ezo rats in a 60-minute open field test.

The hyperactivity of SHRSP/Ezo rats during the exploration phase (0 to 15 minutes) and the habituated phase (15 to 60 minutes) was worsened with methylphenidate (1 mg/kg) as the comparative drug. The subcutaneous administration of BPAP (0.01 to 0.3 mg/kg) significantly inhibited the increase in behavior at the habituated phase was without affecting the locomotor activity at the exploration phase with a dose of 0.01 to 0.1 mg/kg. BPAP at 0.3 mg/kg, however, had no action against the locomotor activity at the exploration and the habituated phase (FIG. 2).

Figure 3:
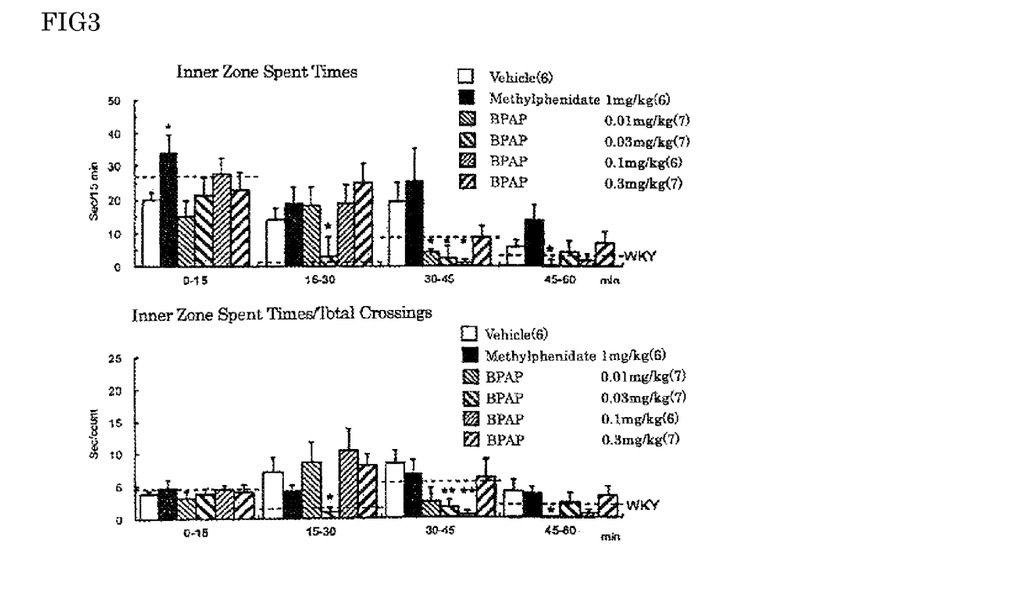
FIG. 3 shows the effects of the compound for use in the invention on increases of the inner zone spent time in SHRSP/Ezo rats in an open field test in the upper panel and the inner zone spent times per total crossings in the lower panel.

Since the spent time in the inner zones (nine compartments in the center) (inner zone spent time) in the open field test is used for the evaluation of the anxiety level, the spent times per time (sec/15 min) and per behavior (sec/count) corrected with the locomotor activity (total crossings) were analyzed as the secondary evaluation in the open field test (FIG. 3). Since animals normally exhibit, from anxiety, a nature of walking in a peripheral zone keeping a touch with a sidewall of the device (thigmotaxis), they little exhibit exploration behaviors into the inner zone. SHRSP/Ezo rats show an increase in spent time in the inner zone at the habituated phase during which hyperactivity was observed, indicating a reduction in anxiety level at the habituated phase. Methylphenidate (1 mg/kg) significantly increased the spent time in the inner zone at the exploration phase, and had no effect on the reduction in anxiety level at the habituated phase. BPAP (0.01 to 0.1 mg/kg) significantly reduced the inner zone spent time at the habituated phase, suggesting the possibility of amelioration of reduced level of anxiety. However, 0.3 mg/kg of BPAP had no effect on the reduction in anxiety level at habituated phase.

2-3) Elevated-Plus Maze Test

Figure 4:
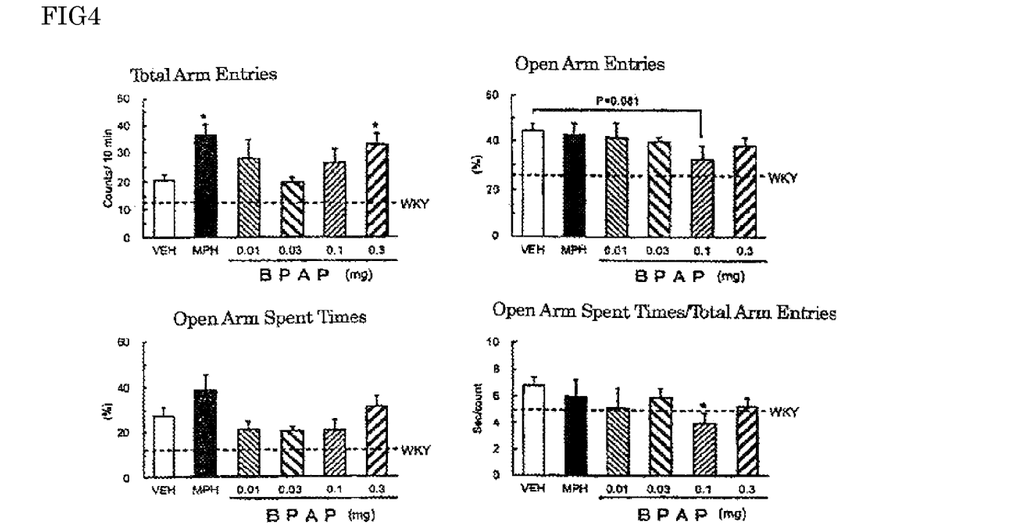
FIG. 4 shows the effects of the compound for use in the invention on the total arm entries (upper left), the rate of open arm entries (upper right), the open arm spent times (lower left), and the time spent in open arms/total number of arm entries (lower right) in a 10-minite elevated-plus maze test using SHRSP/Ezo rats.

In the evaluation of the impulsivity based on an anxiety-related behavior in the elevated-plus maze test, methylphenidate (1 mg/kg) significant worsened the increase in the total number of arm entries, i.e., exacerbation of the hyperactivity in SHRSP/Ezo rats. It did not improve the increase in the rate of open arm entries and the extension of the spent time on the open arms. The compound for use in the invention (0.01 to 0.3 mg/kg) had no effect on the extension of the spent time on the open arms, but it had a tendency to reduce the rate of open arm entries with a dose of 0.1 mg/kg (P=0.08). BPAP at 0.1 mg/kg significantly reduced the spent time on the open arms per total number of arm entries performed as the secondary analysis (FIG. 4).

INDUSTRIAL APPLICABILITY

From the above test results, the possibility is shown that the prophylactic or therapeutic agent for ADHD according to the invention may exert an effect on impulsivity more than methylphenidate can do, and it is expected that the therapeutic effect may be exerted even on a methylphenidate-ineffective case. Also, it has become evident that the prophylactic or therapeutic agent for ADHD according to the invention exhibits an inhibition action against a methamphetamine-seeking behavior in rats (due to drug-associated cues and methamphetamine-priming) and an effective dose of the compound for use in the invention did not induce the methamphetamine-seeking behavior. As for the dependence liability of the prophylactic or therapeutic agent for ADHD according to the invention, the possibility of not creating strong dependence liability with at least a therapeutic dose has been shown. Also, while it takes time for atomoxetine to produce a stable drug efficacy, the prophylactic or therapeutic agent for ADHD according to the invention, which has the central stimulation action, is a promising drug of a type producing the efficacy as rapidly as or more rapidly than methylphenidate.

From the above findings, the prophylactic or therapeutic agent for ADHD according to the invention has an efficacy spectrum different from the existing ADHD therapeutic drugs such as methylphenidate and atomoxetine, and is expected to expand the options of the drug therapy for ADHD by being used alone or in combination with other ADHD therapeutic drugs.

The invention claimed is:

1. A therapeutic method for attention-deficit/hyperactivity disorder comprising administering an effective dose of 1-(benzofuran-2-yl)-2-propylaminopentane or a pharmacologically acceptable acid addition salt thereof to a patient suffering from attention-deficit/hyperactivity disorder.

2. The therapeutic method for attention-deficit/hyperactivity disorder according to claim 1, wherein said effective dose of 1-(benzofuran-2-yl)-2-propylaminopentane or a pharmacologically acceptable acid addition salt thereof is from 1 mg/day to 500 mg/day.

3. The therapeutic method for attention-deficit/hyperactivity disorder according to claim 2, wherein 1-(benzofuran-2-yl)-2-propylaminopentane is (−)-1-(benzofuran-2-yl)-2-propylaminopentane.

4. The therapeutic method for attention-deficit/hyperactivity disorder according to claim 1, wherein the 1-(benzofuran-2-yl)-2-propylaminopentane or a pharmacologically acceptable acid addition salt thereof is used in combination with one or more other therapeutic agents for attention-deficit/hyperactivity disorder selected from the group consisting of methylphenidate, atomoxetine, amphetamine, dextroamphetamine, lisdexamfetamine, guanfacine, clonidine, and bupropion.

\* \* \* \* \*